United States Patent
Ha

(10) Patent No.: US 10,041,963 B2
(45) Date of Patent: Aug. 7, 2018

(54) SYSTEM FOR ADJUSTING AUTOMATIC ANALYSIS, METHOD FOR ADJUSTING AUTOMATIC ANALYSIS

(71) Applicant: HITACHI HIGH-TECHNOLOGIES CORPORATION, Tokyo (JP)

(72) Inventor: Chikook Ha, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 274 days.

(21) Appl. No.: 14/377,304

(22) PCT Filed: Feb. 8, 2013

(86) PCT No.: PCT/JP2013/053117
§ 371 (c)(1),
(2) Date: Aug. 7, 2014

(87) PCT Pub. No.: WO2013/122013
PCT Pub. Date: Aug. 22, 2013

(65) Prior Publication Data
US 2015/0029331 A1    Jan. 29, 2015

(30) Foreign Application Priority Data
Feb. 16, 2012    (JP) .................................. 2012-031557

(51) Int. Cl.
*G01N 35/00*    (2006.01)
*G06T 7/00*    (2017.01)
(Continued)

(52) U.S. Cl.
CPC .  *G01N 35/00594* (2013.01); *G01N 35/00732* (2013.01); *G01N 35/1011* (2013.01);
(Continued)

(58) Field of Classification Search
CPC ........... G06T 2207/30148; G06T 7/001; G06T 7/0002; G06T 7/204; G06T 7/2053;
(Continued)

(56) References Cited

U.S. PATENT DOCUMENTS 4,586,546 A * 5/1986 Mezei ................ G01N 35/1011
141/2
5,232,669 A * 8/1993 Pardinas ............... B01L 3/0275
206/562

(Continued)

FOREIGN PATENT DOCUMENTS

EP          1564542 A1    8/2005
JP      2003-145004 A    5/2003
(Continued)

OTHER PUBLICATIONS

Uber, D. C., Jaklevic, J. M., Theil, E. H., Lishanskaya, A., & McNeely, M. R. (1990). "Application of Robotics and Image Processing to Automated Colony Picking and Arraying." Biotechniques, 11(5), 642-647.—Report Number: LBL-29870 (Year: 1990).*

(Continued)

*Primary Examiner* — Jorge L Ortiz Criado
*Assistant Examiner* — Daniel Chang
(74) *Attorney, Agent, or Firm* — Mattingly & Malur, PC

(57) ABSTRACT

Various mechanisms of an automatic analysis device are adjusted to suppress the occurrence of a difference in adjustment quality between an experienced person and an inexperienced person. An adjustment system includes a current position information acquiring unit for acquiring information indicating a current position of an adjustment object, a predetermined position information storage unit preliminarily storing information indicating a predetermined position where the adjustment object should be located and an (Continued)

adjustment value calculation unit which, by comparing the information indicating the current position of the adjustment object acquired by the current position information acquiring unites with information indicating the predetermined position of the adjustment object that has been stored in the predetermined position information storage unit, calculates an adjustment value that is required for adjusting the position of the adjustment object from the current position to the predetermined position.

14 Claims, 11 Drawing Sheets

(51) Int. Cl.
 *G01N 35/10* (2006.01)
 *G01N 35/04* (2006.01)
(52) U.S. Cl.
 CPC ...... *G06T 7/001* (2013.01); *G01N 2035/0494* (2013.01); *G06T 7/0002* (2013.01)
(58) Field of Classification Search
 CPC ... G06T 7/0024; G06T 7/0044; G06T 7/0028; H04N 5/23254; H04N 5/23267; H04N 13/026; G01N 21/95607; G01N 35/1011; A01G 7/00; G02B 6/3807; H01L 21/67796; H01L 21/68; B01L 3/0279; B01L 3/0275; B25J 9/107; B25J 9/1697; G03F 9/7003; G01B 11/26; G05B 19/41875
 USPC ....... 382/149, 294, 141, 145, 199, 295, 130, 382/208.4, 110, 151; 348/95, 43; 356/73.1, 138; 700/228, 258, 245, 114; 73/864.14; 141/2; 206/562; 422/501; 318/568.11; 438/14
 See application file for complete search history.

(56) References Cited

U.S. PATENT DOCUMENTS

| | | | | |
|---|---|---|---|---|
| 5,268,733 | A * | 12/1993 | Wright | G01B 11/26 356/138 |
| 5,321,353 | A * | 6/1994 | Furness | B25J 9/1697 318/568.11 |
| 5,729,622 | A * | 3/1998 | Csipkes | G02B 6/3807 356/73.1 |
| 9,255,939 | B2 | 2/2016 | Nishida et al. | |
| 9,494,610 | B2 | 11/2016 | Yamamoto et al. | |
| 2001/0053245 | A1 * | 12/2001 | Sakai | G01N 21/95607 382/151 |
| 2002/0103571 | A1 * | 8/2002 | Yoo | H01L 21/67796 700/228 |
| 2003/0111494 | A1 | 6/2003 | Lin et al. | |
| 2004/0267405 | A1 * | 12/2004 | Ingenhoven | B25J 9/1692 700/245 |
| 2005/0180608 | A1 * | 8/2005 | Tanabata | A01G 7/00 382/110 |
| 2006/0105338 | A1 | 5/2006 | Iimura et al. | |
| 2007/0133863 | A1 * | 6/2007 | Sakai | G01N 21/95607 382/151 |
| 2007/0180935 | A1 * | 8/2007 | Angus | B01L 3/0279 73/864.14 |
| 2007/0189596 | A1 * | 8/2007 | Lee | G06T 7/0028 382/151 |
| 2008/0081383 | A1 * | 4/2008 | Chen | G05B 19/41875 438/14 |
| 2008/0144922 | A1 * | 6/2008 | Naiki | G03F 9/7003 382/145 |
| 2009/0062960 | A1 * | 3/2009 | Krishnasamy | B25J 9/107 700/258 |
| 2009/0088887 | A1 * | 4/2009 | Chen | H01L 21/68 700/114 |
| 2012/0262543 | A1 * | 10/2012 | Lee | H04N 13/026 348/43 |
| 2013/0280143 | A1 * | 10/2013 | Zucchelli | B25J 9/1697 422/501 |
| 2017/0059598 | A1 | 3/2017 | Yamamoto et al. | |

FOREIGN PATENT DOCUMENTS

| | | |
|---|---|---|
| JP | 2005-520157 A | 7/2005 |
| JP | 2007-248413 A | 9/2007 |
| JP | 2007-285957 A | 11/2007 |
| JP | 2008-294065 A | 12/2008 |
| JP | 2009-210373 A | 9/2009 |
| JP | 2010-122777 A | 6/2010 |
| WO | 98/18009 A1 | 4/1998 |
| WO | 03/079029 A1 | 9/2003 |
| WO | 2012/014432 A1 | 2/2012 |

OTHER PUBLICATIONS

Anis, Y. H., M. R. Holl, and D. R. Meldrum, "Automated selection and placement of single cells using vision-based feedback control", Automation Science and Engineering, IEEE Transactions on, vol. 7, No. 3: IEEE, pp. 598-606, 2010 (Year: 2010).*

Extended European Search Report received in corresponding European Application No. 13749467.0 dated Sep. 25, 2015.

Japanese Office Action received in corresponding Japanese Application No. 2013-558677 dated May 9, 2017.

* cited by examiner

SYSTEM FOR ADJUSTING AUTOMATIC ANALYSIS, METHOD FOR ADJUSTING AUTOMATIC ANALYSIS

TECHNICAL FIELD

The present invention relates to technique that is used for an automatic analysis device for automatically carrying out an analysis on a sample, and in particular to technique of automatically carrying out adjustments on various mechanisms that compose the automatic analysis device.

BACKGROUND ART

An automatic analysis device that automatically carries out an analysis on a sample such as a sample (specimen) has been known (for example, see Patent Document 1).

Patent Document 1 discloses a system that is provided with a probe formed as a hollow needle capable of moving a liquid sample, a holding plate on which a large number of portions that hold the liquid samples are formed and which is moved relative to the probe and a transparent base on which the holding plate is secured, and which is driven by an actuator.

In the above-mentioned system, the probe is attached to a fluorescent hub, and the hub and probe are designed to be optically discriminable. In the system, a camera for use in picking up an image of fluorescence of the liquid samples held on the holding plate is installed on the side opposite to the probe, with the holding plate and the base interposed therebetween. Moreover, in the system, a technique is disclosed in which an optical marker is placed on the transparent base, and a relative positional relationship between the probe and the base with the holding plate secured thereon is calibrated by allowing the camera to pick up an image of the corresponding marker.

Patent Document 1: Japanese Patent Application Laid-Open Publication (Translation of PCT Application) No. 2005-520157

DISCLOSURE OF THE INVENTION

Problems to be Solved by the Invention

In the above-mentioned automatic analysis device, in order to correctly carry out an analyzing process that is a main process of the analysis device, it is necessary to accurately install the analysis device. The automatic analysis device, which has been produced in a production line during processes from the production of the automatic analysis device to the installation thereof, is disassembled for each of modules, and transported to a customer. The respective modules transferred to the customer are assembled by a service person as the automatic analysis device. After the assembling process, the respective mechanisms are subjected to adjusting and checking processes so as to allow them to execute normal operations as the automatic analysis device.

In this case, the adjustments of the respective mechanisms are different depending on each of the modules. For example, adjustments of 70 portions are required in some cases. Although, at present, the mechanism adjustments are carried out by utilizing software, the corresponding adjustments are carried out by a service person, while the person is directly confirming the adjustments visually. One of the problems of the currently-used adjusting methods for the mechanisms is that there is a difference in the adjustment quality between an experienced person and an inexperienced person and another problem is that there is a time difference from the start of the adjustments to the completion of the adjustments between them.

In view of these problems, the present invention has been devised, and its object is to provide an adjusting technique for various mechanisms of an automatic analysis device, which can suppress a difference in adjustment quality from occurring between an experienced person and an inexperienced person. These and other objects, and novel features of the present invention will become apparent upon consideration of the following description of the preferred embodiments of the present invention taken in conjunction with the accompanying drawing.

Means for Solving the Problems

The following description will briefly discuss the outlines of the typical aspects of the inventions disclosed in the present application.

An adjusting system for an automatic analysis device of the present invention, which forms a part of the automatic analysis device that automatically carries out an analysis on a sample, includes a current position information acquiring unit that acquires information indicating a current position where an object to be adjusted (adjustment object), which is the object a position of which needs to be adjusted, is currently located, a predetermined position information storage unit in which information indicating a predetermined position at which the adjustment object should be positioned is previously stored, and an adjustment value calculation unit which, by comparing the information indicating the current position of the adjustment object that is obtained by the current position information acquiring unit with the information indicating a predetermined position of the adjustment object that is stored in the predetermined position information storage unit, calculates an adjustment value that is a value required for adjusting the position of the adjustment object from the current position to the predetermined position.

In the above-mentioned adjusting system for an automatic analysis device, the current position information acquiring unit is capable of picking up an image of at least one portion of the adjustment object by using a camera, and based upon the image of the adjustment object thus obtained by the image pickup process, and thus capable of acquiring information indicating the current position of the adjustment object.

In the above-mentioned adjusting system for an automatic analysis device, an image indicating the adjustment object that is located at a predetermined position is previously stored in the above-mentioned predetermined position information storage unit as information indicating the predetermined position of the adjustment object, and the adjustment value calculation unit is capable of calculating the adjustment value by comparing an image of the adjustment object that is located at the current position with an image of the adjustment object that is located at the predetermined position.

In the above-mentioned adjusting system for an automatic analysis device, a current position identification mark serving as a mark for use in identifying the current position of the adjustment object is attached to the adjustment object, and the current position information acquiring unit is capable of acquiring information indicating the current position of the adjustment object by picking up the image of the current position identification mark by using a camera.

In the above-mentioned adjusting system for an automatic analysis device, predetermined position identification mark information serving as information corresponding to the current position identification mark information, that is, information for use in identifying the predetermined position of the adjustment object, is previously stored in the predetermined position information storage unit as information indicating a predetermined position of the adjustment object, and the adjustment value calculation unit is capable of calculating the adjustment value by comparing the position of the current position identification mark in the current position image thus picked up and the information indicating the current position identification mark in the predetermined position image previously stored.

Moreover, an adjusting method for an automatic analysis device in accordance with the present invention, which forms an automatic analysis device for automatically carrying out an analysis on a sample by using a computer, includes a step of acquiring information indicating a current position where an adjustment object, which is the object a position of which needs to be adjusted, is currently located, and a step of, by comparing the information indicating the current position of the adjustment object that has been acquired with the information indicating a predetermined position where the adjustment object should be located, which is stored in the predetermined position information storage unit, calculating an adjustment value that is a value required for adjusting the position of the adjustment object from the current position to the predetermined position.

Effects of the Invention

Of the inventions disclosed by the present application, the following description will briefly discuss effects obtained by those typical inventions of them.

It becomes possible to suppress the occurrence of a difference in quality of adjustments between an experienced person and an inexperienced person and the occurrence of a time difference in a period from the start of adjustments to the completion of the adjustments between those persons.

BRIEF DESCRIPTIONS OF THE DRAWINGS

Figure 6:
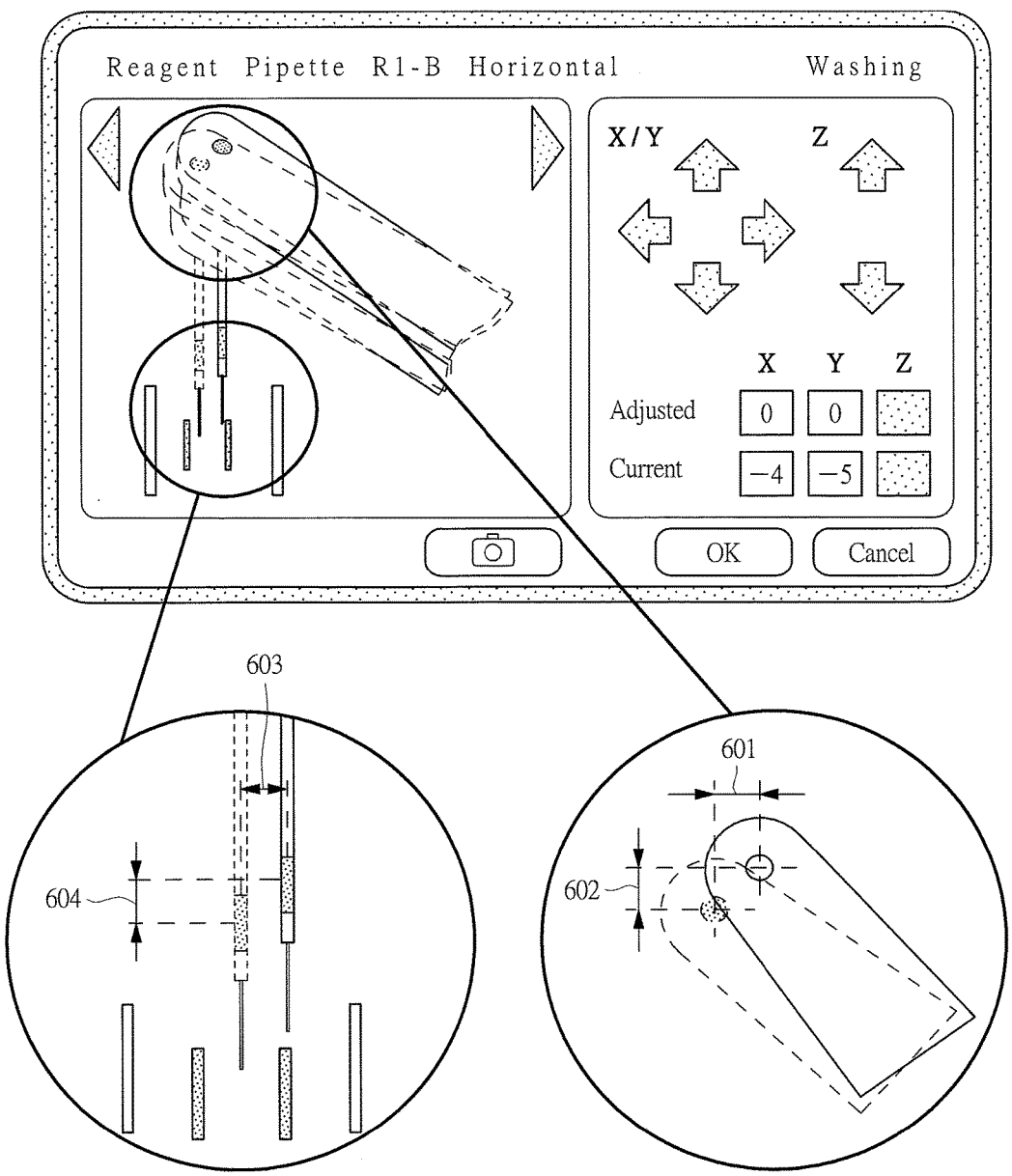
Figure 7:
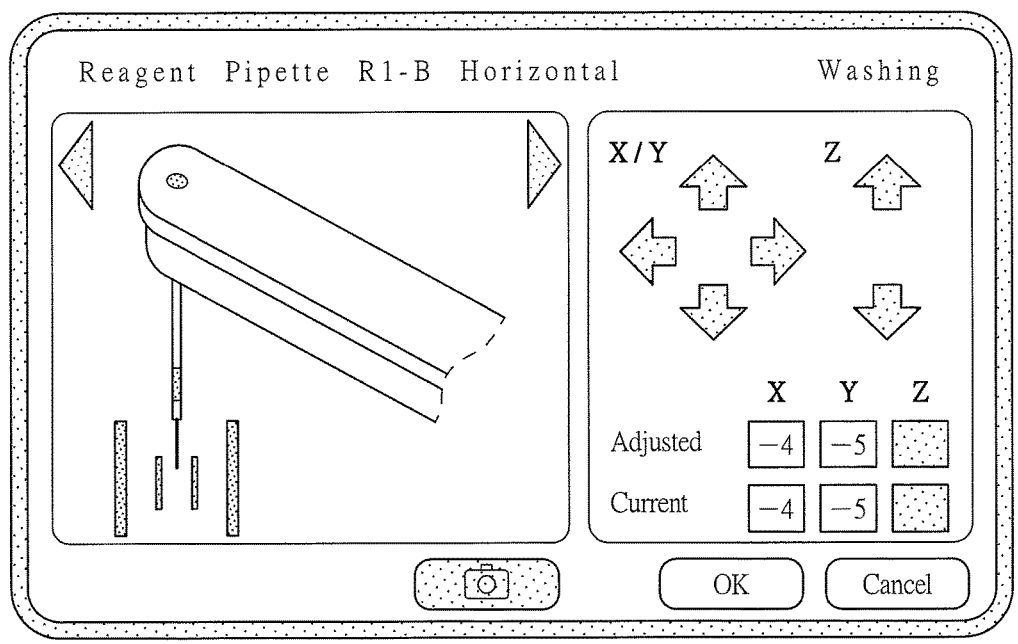

FIG. 6 is a diagram illustrating a screen picking up images of the mechanism to be adjusted and the portion to be adjusted, and explains in detail a process for measuring a differential distance between the predetermined position of the mechanism to be adjusted and the mechanism to be adjusted so as to obtain an adjustment value; and FIG. 7 is a diagram illustrating one example of a screen at the time of adjustment completion, which is displayed when the adjustment value is stored in the automatic analysis device and the adjustment system.

BEST MODE FOR CARRYING OUT THE INVENTION

Referring to Figures, the following description will discuss embodiments in accordance with the present invention (hereinafter, referred to simply as "embodiments") in detail. Additionally, the present invention is not limited to the following embodiments, and various modifications can be made within the range of the gist of the present invention.

Figure 1A:
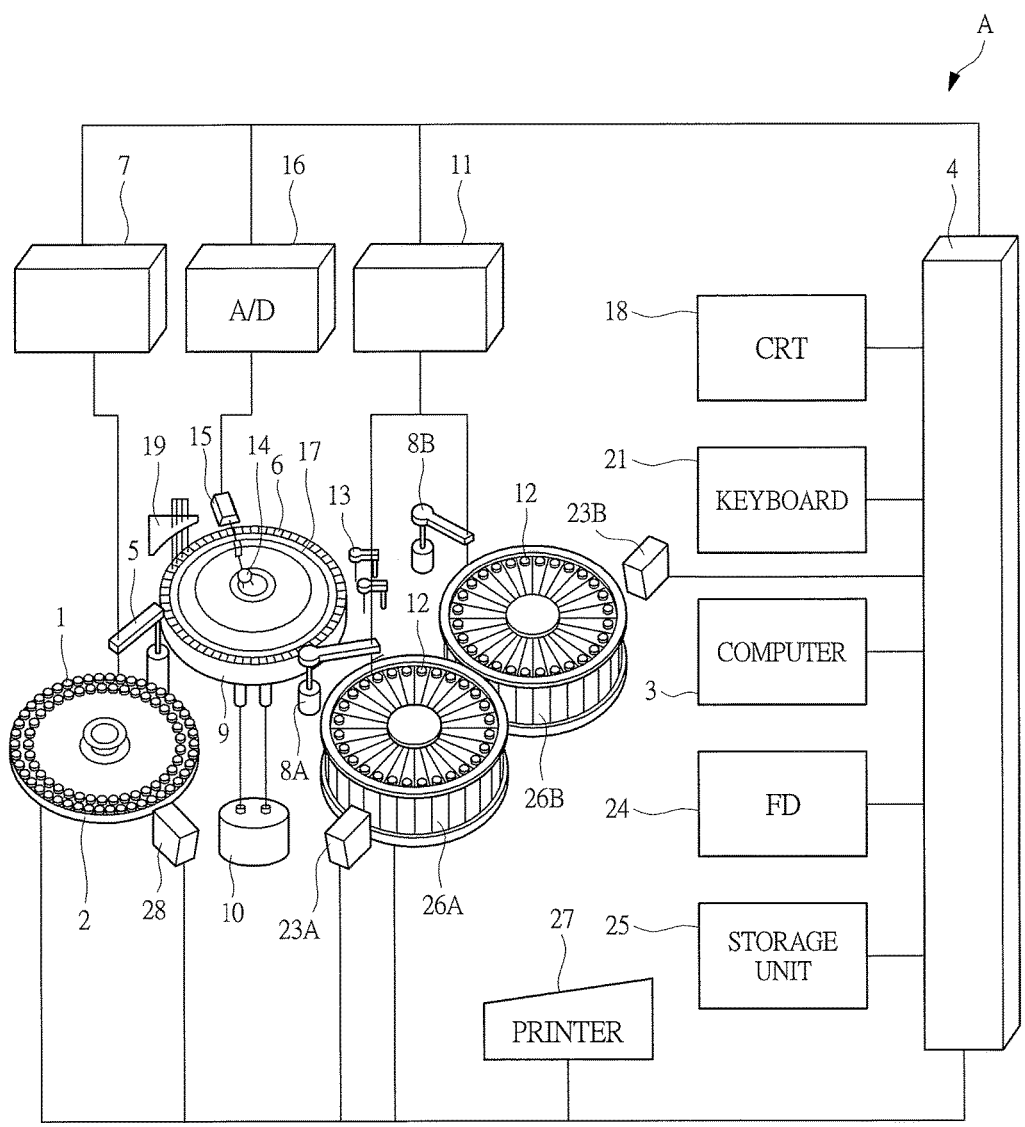
FIG. 1A is an entire constitution diagram illustrating a multiple chemical automatic analysis device.
Figure 1B:
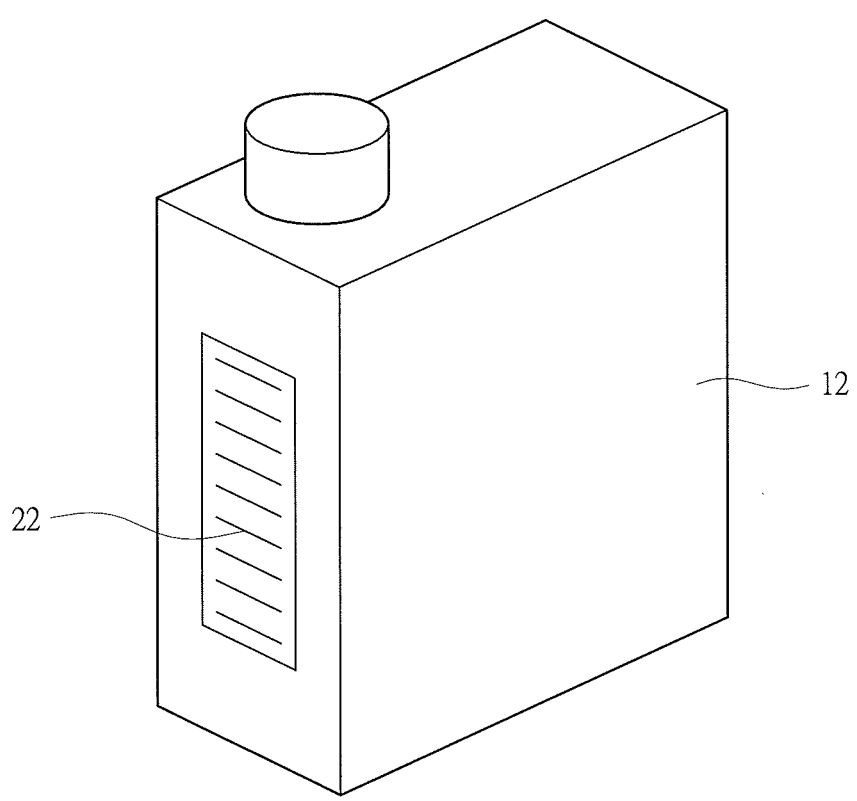
FIG. 1B is an external diagram of a reagent bottle to which a reagent barcode label is pasted.
Figure 1C:
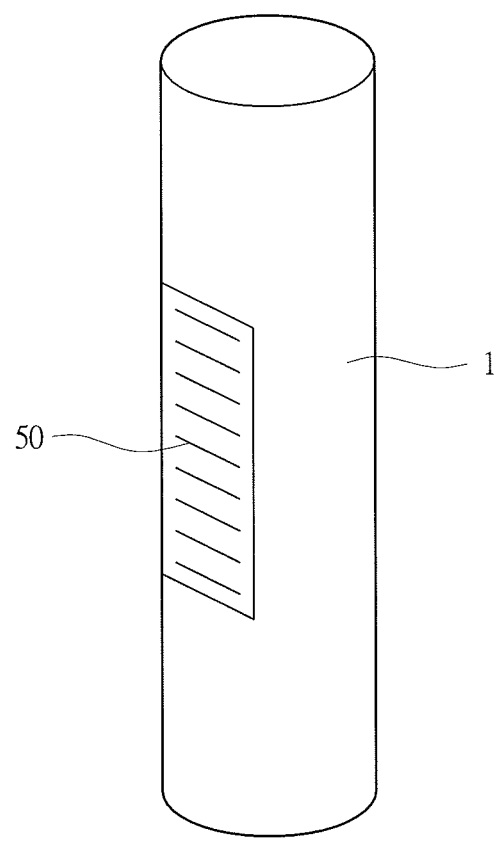
FIG. 1C is an external diagram of a sample cup to which a sample barcode label is pasted.

FIG. 1A is an entire constitution diagram illustrating a multiple chemical automatic analysis device. FIG. 1B is an external diagram of a reagent bottle to which a reagent barcode label is pasted. FIG. 1C is an external diagram of a sample cup to which a sample barcode label is pasted.

In FIG. 1A, a large number of sample cups 1 in which samples are housed are arranged on a sample transporting disc 2. A suction/discharge nozzle of a sample aliquot mechanism 5 is connected to a sample-use syringe pump 7. Operations of the sample-use syringe pump 7 and the aliquot mechanism 5 are controlled by a microcomputer 3 that executes an operation control of each of the mechanisms and a computing process of measured data through an interface 4.

On a reaction table 17 attached to a reaction bath 9 so as to rotate thereon, a large number of reaction cuvettes 6 are arranged so that a reaction line is formed. A constant temperature liquid maintained at 37 degrees Celsius is supplied from the constant-temperature liquid supply unit 10 to the reaction bath 9. A multi-wavelength photometer is provided with a light source 14 and a multi-wavelength spectroscope 15, and the reaction table 17 is rotated and transferred in a manner so as to allow the row of the reaction cuvettes 6 to traverse an optical beam from the light source 14. The reaction cuvettes 6 that have been used are rinsed by a rinse mechanism 19, and reused.

A stirring mechanism 13 mixes the sample added to the reaction cuvette 6 with a reagent liquid corresponding to its analysis item. A measurement signal, which is obtained by the multi-wavelength spectroscope 15 based upon the reaction liquid, is converted from an analog signal to a digital signal by an A/D converter 16, and inputted to the microcomputer 3.

On each of a first reagent-use reagent disc 26A and a second reagent-use reagent disc 26B, various kinds of reagent bottles 12 corresponding to various analysis items are disposed along its circumference. In other words, the discs 26A and 26B form reagent bottle housing units that can be selectively rotated. In the vicinity of the disc 26A, a barcode reading device 23A is disposed. In the vicinity of the disc 23B, a barcode reading device 23B is disposed A reagent aliquot device includes reagent aliquot pipetters 8A and 8B and a reagent-use syringe pump 11. Each of these pipetters 8A and 8B sucks a predetermined amount of a reagent liquid inside the reagent bottle 12 stopped at a suction position into the suction/discharge nozzle so as to be maintained therein, and the suction/discharge nozzle discharges the reagent liquid maintained therein into the reaction cuvette 6 pivoted onto the row of the reaction cuvettes and stopped at a reagent receiving position. The reagent liquid to be aliquoted at this time is that of a kind corresponding to an analysis item assigned to each of the reaction cuvettes.

As illustrated in FIG. 1B, a reagent barcode label 22 on which a barcode is printed is pasted onto an outer wall of each of the reagent bottles 12. Information displayed as this barcode includes, for example, a reagent bottle code inherent to each bottle, which is indicated by a sequential number, the size of the bottle, the effective period of the reagent, the reagent aliquot order indicating the first, second or third reagent, the maximum analyzable number of the reagent liquid, the reagent aliquot amount indicating the aliquot amount of use at one time, the production lot number, and the like.

The reagent information read by the barcode reading device 23A or 23B from each of the reagent bottles 12 is stored in each of corresponding memory areas in the storage unit 25 or the microcomputer 3. In response to the housing process of the reagent bottle 12 in the reagent disc 26A or 26B, the reagent information is read by the barcode reading device 23A or 23B. In this case, a signal indicating the set position of each of the reagent bottles is outputted by a rotation angle detection unit attached to each of the reagent discs, and inputted to the microcomputer 3 through the interface 4. The reagent information, the bottle set position and the analysis item are stored in a manner so as to be associated with one after another.

An operator is allowed to input various pieces of information by using a screen of CRT 18 and a keyboard 21. The measurement results of each of the analysis items can be displayed on a printer 27 and the CRT 18. The information of a floppy (registered trademark) disk (referred to also as a flexible disk) 24 is read by the reading device, and stored in the corresponding memory area of the storage unit 25 or the microcomputer 3.

The information stored in the floppy (registered trademark) disk 24, for example, includes the following pieces of information. That is, analysis item codes, each indicated by 5 digits, parameters commonly used in the analysis items, parameters individually stored for each of the reagent bottles and the like, are included. Among these, as the parameters commonly used in the corresponding analysis item, a wavelength for use in a photometer, a sample amount, a calibration method, a standard solution concentration, the number of standard solutions, a check limitation value of abnormal analysis and the like can be listed.

Moreover, as the parameters for each of the reagent bottles, a reagent type, the order of reagent aliquots, reagent bottle codes, reagent liquid capacities, reagent aliquot amounts, the maximum number of analyzable times, the reagent production date and the like are listed.

In addition to the information read from the floppy (registered trademark) disk 24, in the storage unit 25, operation conditions of the respective mechanisms of the automatic analysis device A, analysis parameters of the respective analysis items, judgment logic for use in carrying out bottle managements of each of the reagents, the maximum number of analyzable times read from the reagent bottle, the results of analysis and the like are stored. The reagent information is supplied by the floppy (registered trademark) disk provided by the maker at the time of the delivery of a reagent bottle.

In the case when no reagent information is prepared by the floppy (registered trademark) disk, the operator may input information described on a visually confirming paper attached to the reagent bottle to the automatic analysis device A by using the screen of the CRT 18 and the keyboard 21.

As illustrated in FIG. 1C, on the sample cup 1, a sample barcode label 50 on which a barcode is printed is pasted onto its outer wall. Information displayed as the barcode is, for example, a sample type number that uniquely determines the sample. The number is read by the barcode reading device 28, and by using the angle detection of the sample transporting disc 2, the corresponding relationship between the sample position and the sample type number can be recognized.

On the other hand, since an analysis item corresponding to the sample type number has been previously inputted and stored by the keyboard 21 and the CRT 18, the sample position, the sample type number and the analysis item are finally stored in association with one after another at the time of previously reading the barcode. Moreover, it is generally designed to be distinguishable whether the corresponding sample is a standard sample or a control sample based upon the higher number of the sample type number.

The analysis of the entire automatic analysis device A is executed in the order of the sampling process, reagent aliquoting process, stirring process, light measuring process, rinsing process of the reaction cuvette and data processing process of the concentration conversion or the like, as will be described below. A plurality of the sample cups 1 to which the sample is added are disposed on the sample disc 2. The sample disc 2 is controlled by the computer 3 through the interface 4.

Moreover, the sample disc 2 allows the barcode reading device 28 to read the barcode 50 on the outer wall of the sample cup 1 so that the sample and the analysis item are made in association with each other. Thereafter, in accordance with the order of samples to be analyzed, it is rotated and moved under the probe of the sample aliquot mechanism 5 so that a predetermined amount of the sample of the predetermined sample cup 1 is aliquoted into the reaction cuvette 6 by operations of the sample-use syringe pump 7 coupled to the sample aliquot mechanism 5.

The reaction cuvette 6 with the sample aliquoted therein is moved up to a first sample adding position through the inside of the reaction bath 9. To the reaction cuvette 6 thus moved, a predetermined amount of a reagent sucked from the reagent cuvette 12 is added by operations of the reagent-use pump 11 coupled to the suction/discharge nozzle of each of the reagent aliquot pipetters 8A and 8B. After the addition of the first reagent, the reaction cuvette 6 is moved to the position of the stirring mechanism 13, and subjected to a first stirring process. In the case when the first to fourth reagents have been set on the reagent discs 26A and 26B, these adding to stirring processes of the reagent are carried out on the first to fourth reagents.

The reaction cuvette 6 contents of which have been stirred allows a light beam emitted by the light source to pass therethrough, and the absorbance at this time is detected by the multi-wavelength spectroscope 15. An absorbance signal thus detected is put into the computer 3 through the interface 4 by way of an A/D converter 16, and is then converted to a sample concentration. Data thus converted into the concentration are outputted and printed by a printer 27 through the interface 4, and displayed on the screen of the CRT 18.

The reaction cuvette 6 that has been subjected to the photometric process is moved to the position of the rinsing mechanism 19, and after the contents thereof have been discharged by a cuvette rinsing pump, it is rinsed by a rinsing solution, and subjected to the next analysis.

In the automatic analysis device A as described above, in order to correctly carry out the analyzing process that is the main process of the corresponding analysis device, an accurate installing process of the analysis device is required. The automatic analysis device A, which has been produced in a production line during processes from the production of the automatic analysis device A to the installation thereof, is disassembled for each of modules, and transported to a customer.

The respective modules transferred to the customer are assembled by a service person as the automatic analysis device A. After the assembling process, the respective mechanisms are subjected to adjusting and checking processes so as to allow them to execute normal operations as the automatic analysis device A. In this case, although different depending on each of the modules, about 20 or more portions of the mechanisms, such as the sample aliquot mechanism, the reagent aliquot mechanism, the reagent disc mechanism, a cell rinsing mechanism, the reagent transporting mechanism, the sample transporting mechanism, a reagent loader mechanism and the like, need to be adjusted.

Moreover, there are a plurality of adjustment positions in each of the mechanisms, and in some cases, the adjustment positions of about 70 portions are required. Although, at present, the mechanism adjustments are carried out by utilizing software, the corresponding adjustments are carried out by a service person, while the person is directly confirming the adjustments visually. One of the problems of the currently-used adjusting methods for the mechanisms is that there is a difference in the adjustment quality between an experienced person and an inexperienced person and another problem is that there is a time difference from the start of the adjustments to the completion of the adjustments between them.

Figure 1D:
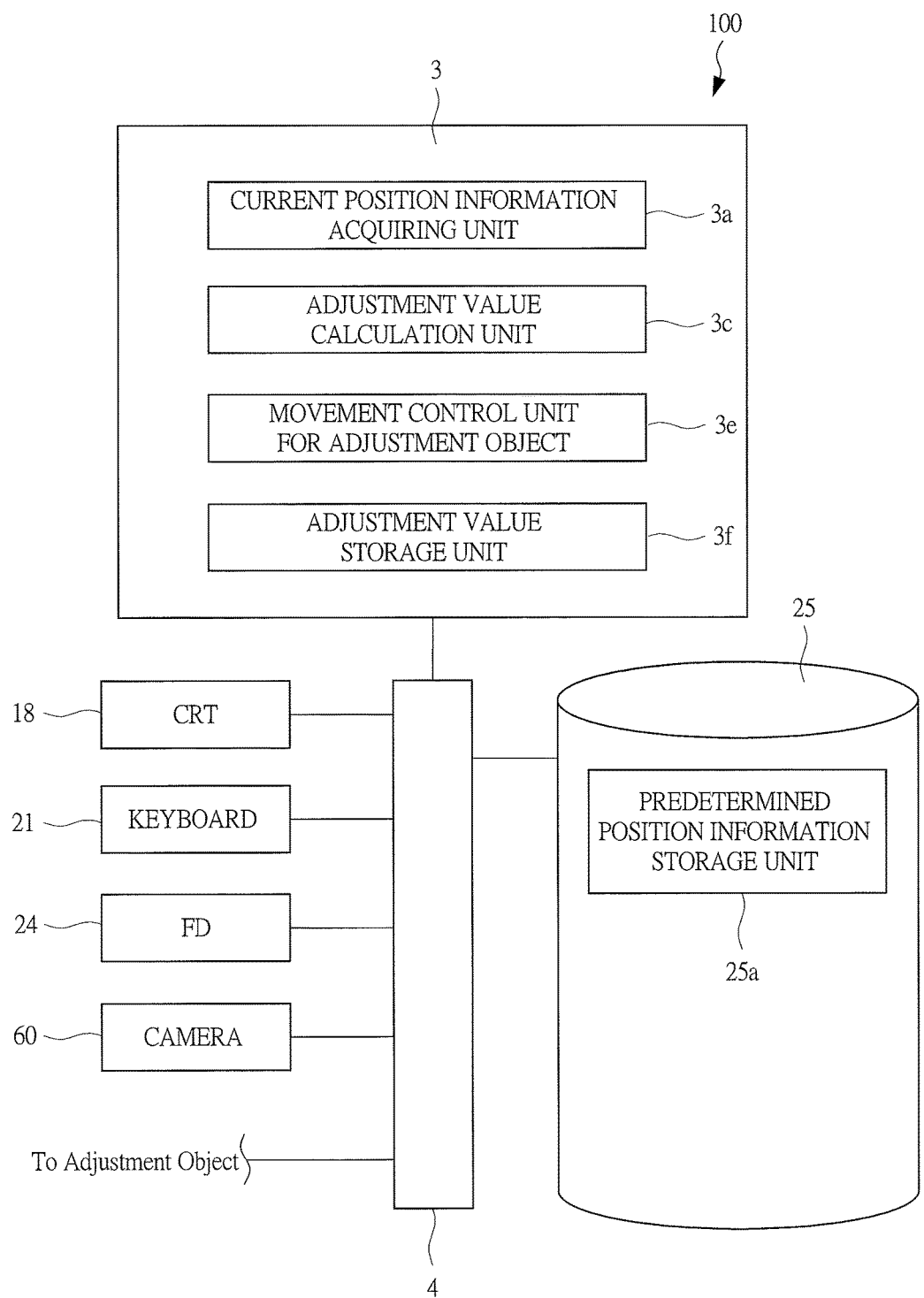
FIG. 1D is a schematic diagram illustrating one example of a hardware configuration of an adjustment system for the automatic analysis device of the present embodiment.

Therefore, in the automatic adjustment system of the automatic analysis device A in accordance with the present embodiment, based upon information indicating a position (hereinafter, referred to simply as "current position") where "an adjustment object" that is an object a position of which needs to be adjusted is currently located and information indicating a predetermined position (hereinafter, referred to simply as "predetermined position") where the adjustment object should be located, an adjustment value from the current position to the predetermined position is calculated, and based upon the corresponding adjustment value, the position of the adjustment object is adjusted. Referring to FIG. 1A, FIG. 1D and FIG. 2 to FIG. 7, the following description will discuss the processes in detail. FIG. 1D is a schematic diagram showing a hardware configuration of the automatic adjustment system of the automatic analysis device in accordance with the present embodiment.

Additionally, among objects constituting the automatic analysis device, the "adjustment object" includes a mechanism a position of which needs to be adjusted by a service person so as to provide normal operations as the automatic analysis device after the automatic analysis device has been assembled at the customer (hereinafter, referred to simply as "a mechanism to be adjusted"). Moreover, the "adjustment object" includes a position and a portion which need to be position-adjusted so as to allow the above-mentioned mechanism to be adjusted to access thereto (hereinafter, referred to as "portion to be adjusted").

The mechanism to be adjusted includes, for example, the suction/discharge nozzle, the sample aliquot mechanism 5, the reagent aliquot pipetters 8A and 8B, the first reagent-use reagent disc 26A, the second reagent-use disc 26B and the like. There are a plurality of portions to be adjusted with respect to one mechanism to be adjusted.

For example, in FIG. 1A, the reagent pipetter 8A, which is a mechanism to be adjusted, sucks a reagent from the reagent bottle 12, and pours the reagent into the reaction cuvette 6. In this case, the portions to be adjusted of the reagent aliquot pipetter 8A correspond to portions (positions) to which the reagent aliquot pipetter 8A accesses, that is, the reagent bottle 12 and the reaction cuvette 6. Additionally, a specific determination method for the adjustment value will be explained later.

As illustrated in FIG. 1D, in an adjustment system 100 in the automatic analysis device, the aforementioned microcomputer (hereinafter, referred to simply as "computer") 3 is installed as an operation processing device that not only carries out operation controls on the respective mechanisms and computing operations on measured data as described earlier, but also further carries out various kinds of computing operations relating to adjustments of the objects to be adjusted (mechanisms to be adjusted and portions to be adjusted).

Additionally, the computer 3 includes a random access memory (RAM) serving as a main storage device, not illustrated. In addition, the aforementioned keyboard 21 is attached to the adjustment system 100 as an input device that allows an adjustment worker, such as a service person or the like, to input various kinds of information into the computer 3.

Moreover, the adjustment system 100 is further provided with the aforementioned CRT 18 as a display device for displaying various kinds of information computed by the computer 3 to the adjustment worker. Furthermore, in the adjustment system 100, the aforementioned storage unit (ROM) 25 and floppy (registered trademark) disk 24 are installed as auxiliary storage devices in which various kinds of information relating to adjustments for the adjustment object are previously stored.

Moreover, in the adjustment system 100 of the automatic analysis device, a camera 60 is installed as an image-pickup device for picking up images of objects to be adjusted (mechanisms to be adjusted or portions to be adjusted). Additionally, a plurality of cameras 60 may be installed in accordance with the objects to be adjusted.

Furthermore, in the adjustment system 100, the computer 3 serving as the operation processing device, the CRT 18 serving as the display device, the keyboard 21 serving as the input device, the floppy (registered trademark) disk 24 serving as the auxiliary storage device and the storage unit (ROM) 25, as well as the camera 60 serving as the image-pickup device, are designed such that various kinds of information can be inputted thereto or outputted therefrom through the aforementioned interface.

An image of the adjustment object picked up by the camera 60 is acquired by the main storage device (RAM) of the computer 3 through the interface 4. The image of the adjustment object is analyzed by the computer 3. Moreover, the computer 3 of the adjustment system 100 is designed so that based upon the result of the analysis of the image to be adjusted, it can adjust the position of the adjustment object (the mechanism to be adjusted and portion to be adjusted) through the interface 4.

Additionally, in the present embodiment, the adjustment system 100 of the automatic analysis device A is designed to commonly use the computer 3 serving as the operation processing device, the CRT 18 serving as the display device, the keyboard 21 serving as the input device, the floppy (registered trademark) disk 24 serving as the auxiliary storage device and the storage unit (ROM) 25 with the automatic analysis device A; however, the hardware configuration of "the adjustment system" relating to the present invention is not intended to be limited by this mode.

For example, separately from the computer 3, CRT 18, keyboard 21, floppy (registered trademark) disk 24 and the storage unit (ROM) 25 constituting the automatic analysis device A, an operation processing device, an input device, a display device and an auxiliary storage device, which are exclusively used for the adjustment system, may be installed.

Additionally, "the adjustment system" relating to the present invention may be realized by using a generally used portable computer. For example, by allowing a generally used portable terminal device (computer) with a camera to communicate with the computer 3 of the automatic analysis device A, "the adjustment system" of the present invention may be desirably realized.

Moreover, "the current position" refers to a position of the adjustment object (that is, the mechanism to be adjusted or the portion to be adjusted) at the time after the assembling process of the automatic analysis device at the customer and before the adjustment of the position so as to allow the automatic analysis device to execute normal operations, that is, at the time when the adjustments are carried out. In other words, the position corresponds to a position where the object to be desirably adjusted is located before the adjustment of the position.

Furthermore, "the predetermined position" refers to a correct position where the adjustment object (that is, the mechanism to be adjusted or the portion to be adjusted) should be located so as to allow the automatic analysis device to execute normal operations. In other words, the predetermined position corresponds to a preset position upon designing the automatic analysis device A. The predetermined position of each of various objects to be adjusted that constitute the automatic analysis device is previously set as a value for use in designing the automatic analysis device, and previously stored in the storage unit 25.

Figure 1E:
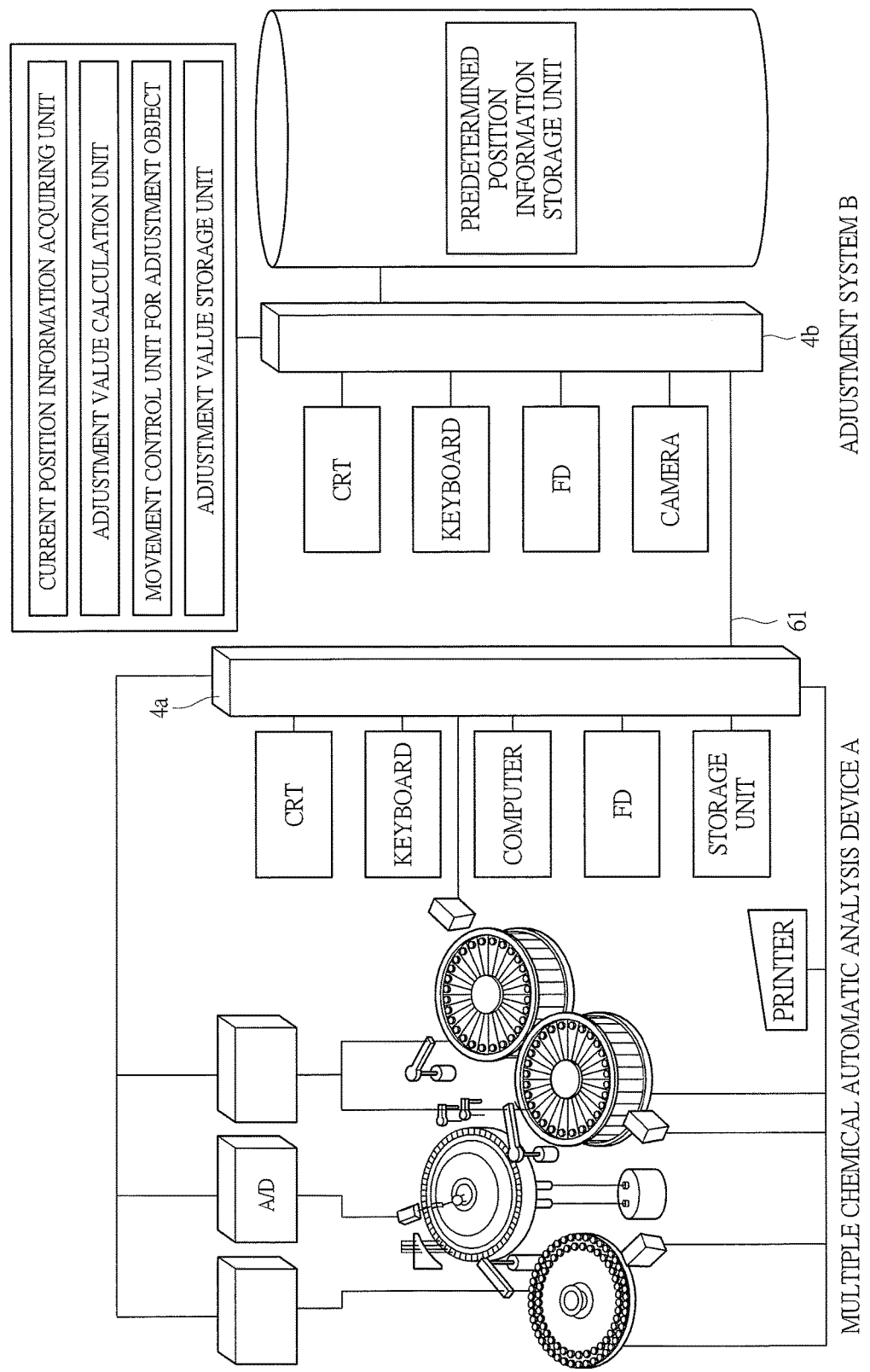
FIG. 1E is a connection constitution diagram of the multiple chemical automatic analysis device and the adjustment system.

FIG. 1E shows a hardware configuration in the case when the multi-purpose chemical automatic analysis device illustrated in FIG. 1A and the adjustment system illustrated in FIG. 1D are connected to each other.

A LAN 61 couples the interface 4a of the multi-purpose chemical automatic analysis device A to the interface 4b of the adjustment system B by cable or radio wave.

The result of analysis of the image to be adjusted picked up by the adjustment system is sent to the computer of the multi-purpose chemical automatic analysis device A through the interface 4a of the multi-purpose chemical automatic analysis device A by way of the interface 4b of the adjustment system B so as to adjust the position of the adjustment object.

Figure 2:
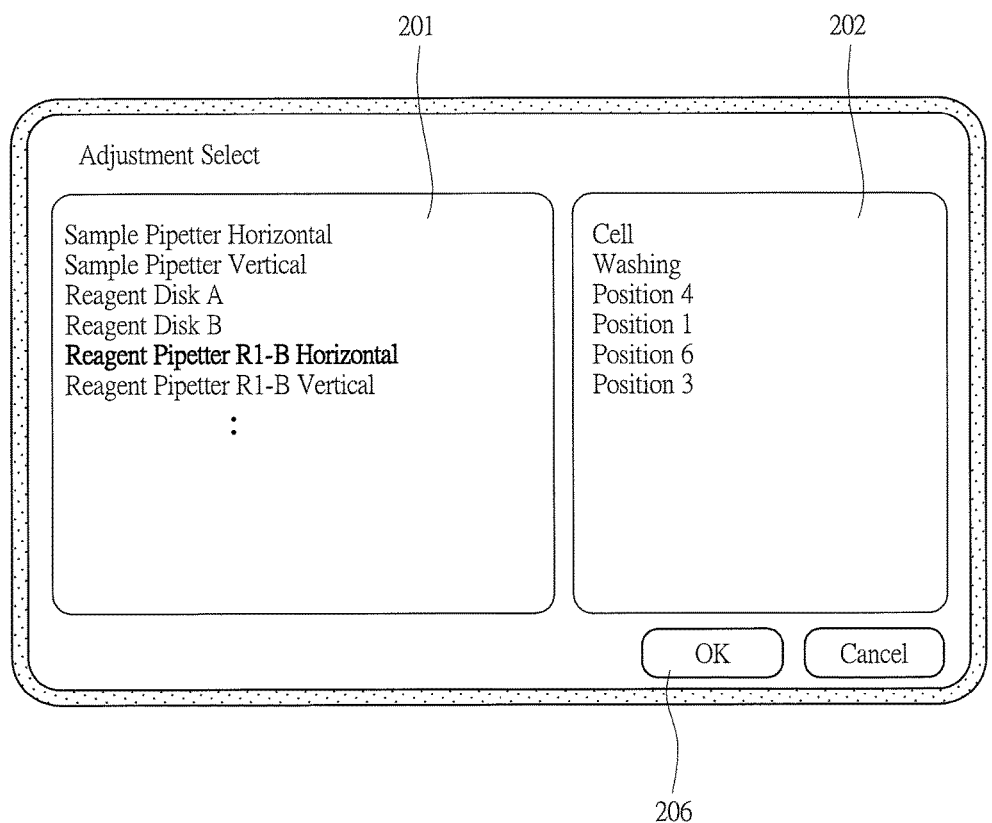
FIG. 2 is a diagram illustrating one example of a selection screen for use in selecting a mechanism to be adjusted, which is one of mechanisms constituting the automatic analysis device and a position of which needs to be adjusted.

FIG. 2 is a diagram illustrating one example of a selection screen for use in selecting a mechanism to be adjusted which forms one portion of the automatic analysis device and whose position is desirably adjusted.

Referring to FIG. 1D and FIG. 2, explanations will be given. A service person (adjustment worker) selects a mechanism of the automatic analysis device A to be desirably adjusted from a list of mechanisms to be adjusted 201 that is displayed on the screen of the CRT 18 by the computer 3. In the present embodiment, "Reagent Pipetter R1-B Horizontal" indicating a horizontal direction adjustment of a reagent aliquot pipetter 8B is selected. By this selection, the computer 3 displays the portion to be adjusted relating to the reagent aliquot pipetter 8B on a list of portions to be adjusted 202 on the screen.

The portion to be adjusted relating to the reagent aliquot pipetter 8B includes "Cell" of the reaction cuvette 6, "Washing" for use in washing the reagent aliquot pipetter, as well as "Position 4", "Position 1", "Position 6" and "Position 3" that correspond to positions (locations) where a reagent from the reagent bottle 12 is aliquoted.

Among these, in the present embodiment, an explanation will be given to the "Washing" portion to be adjusted, which corresponds to the position where the reagent aliquot pipetter is rinsed. When the service person selects a portion to be adjusted by using the keyboard 21 as the input device and presses an OK button 206 on the screen, the computer 3 moves the reagent aliquot pipetter 8B of the automatic analysis device A to the "Washing" position corresponding to the portion to be adjusted, and the sequence waits for an instruction for an adjustment.

Additionally, the "Washing" position refers to a position where the reagent aliquot pipetters 8A and 8B are rinsed. The reagent aliquot pipetters 8A and 8B carryout operations for sucking reagents from the reagent bottles 12 and pouring them into the reaction cuvettes 6; however, in the case when there are a plurality of kinds of reagents, after having been once used for sucking a reagent, the corresponding pipetter needs to be rinsed. Upon rinsing the reagent aliquot pipetters 8A and 8B, the positions to which they are moved correspond to "Washing" positions.

Figure 3:
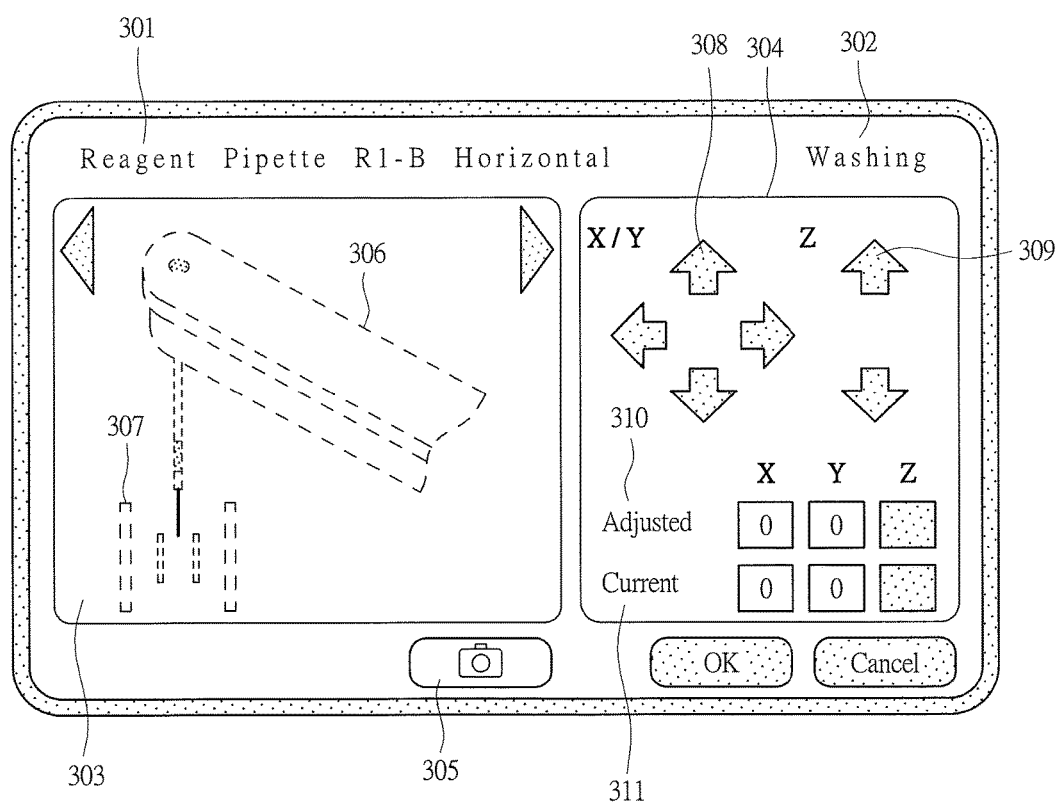
FIG. 3 is a diagram illustrating one example of an adjustment screen for use in adjusting "Washing portion" to be adjusted of a reagent aliquot pipetter which has been selected in the selection screen (FIG. 2) for use in selecting the mechanism to be adjusted.

FIG. 3 is a diagram illustrating one example of an adjustment screen for use in adjusting the "Washing portion" to be adjusted of the reagent aliquot pipetter 8B selected on the screen for selecting the mechanism to be adjusted. Referring to FIG. 1D, FIG. 2 and FIG. 3, explanations will be further given.

The present screen is displayed on the CRT 18 by the computer 3. The computer 3 displays a name 301 of a mechanism to be adjusted, a name 302 of a portion to be adjusted, a predetermined position image display area 303 on which an image indicating a predetermined position of the mechanism to be adjusted/the portion to be adjusted (hereinafter, referred to as a predetermined position image) is displayed, a manual adjustment/adjustment value display area 304 on which an adjustment item or an adjustment value relating to a manual adjustment is displayed, and an image pickup button 305 that allows the camera 60 to pick up an image of the adjustment object.

The computer 3 displays the name of the mechanism to be adjusted 301 corresponding to the name of the mechanism to be adjusted, which has been selected on the selection screen (see FIG. 2) for use in selecting the mechanism to be adjusted on the upper side of the screen of the CRT 18. Thus, the service person can confirm which mechanism to be adjusted at present by using the CRT 18. Moreover, on the right side of the screen of the CRT 18, the computer 3 displays the name of a portion to be adjusted 302, that is, the name of the portion on which the adjustment is carried out at present.

Moreover, on the right side of the adjustment image display area 303 on the screen of the CRT 18, the computer 3 displays arrow keys for use in altering the portion to be adjusted of the mechanism to be adjusted. When the service person presses down a left arrow key, the computer moves the mechanism to be adjusted to a "Cell" portion to be adjusted, which is located on the "Washing" portion to be adjusted, as illustrated in FIG. 2. When the service person presses down a right arrow key, the computer moves the mechanism to be adjusted to a "Position 4" portion to be adjusted, which is located below the "Washing" portion to be adjusted.

In FIG. 3, a predetermined position image 306 of the mechanism to be adjusted and a predetermined position image 307 of the portion to be adjusted indicate a predetermined position of the reagent pipette 8B relative to the predetermined position image (the image of "Washing" position) 307 of the portion to be adjusted. By using these predetermined position images 306 and 307 as standards, the image of the mechanism to be adjusted of the automatic analysis device A to be desirably adjusted, that is, the image (hereinafter, referred to as a current position image) indicating the current position of the adjustment object, and the predetermined position image are compared with each other so as to carry out the adjustment of the adjustment object.

The manual adjustment/adjustment value display area 304 is composed of an X/Y axis adjustment direction key 308, a Z axis adjustment direction key 309, an adjustment value 310 after determination and an adjustment value 311 during the adjustment.

Additionally, "the adjustment value during the adjustment" refers to a temporary adjusted value in the middle of the execution of the adjustment. For example, in the case when the value of X is 7 of the adjustment value (Current) 311 during the adjustment, with the value of X being set to 10 of the adjustment value (Adjusted) 310 after determination, if an attempt is made to manually adjust the predetermined position image 306 by using the X/Y axis adjustment direction key 308, the predetermined position image 306 can be moved in the right direction by 1 pulse by pressing the right arrow button of the X/Y axis adjustment direction key 308 by one time, with the value of X of the adjustment value 311 during the adjustment being increased from 7 to 8.

From this state, when the right arrow button of the X/Y axis adjustment direction key 308 is further pressed down one time, the predetermined position image 306 can be further moved in the right direction by 1 pulse, with the value of the adjustment value 311 during the adjustment being increased from 8 to 9. When this value is determined, the value of X of the adjustment value 310 after determination becomes 9 from 10. The adjustment value 310 after determination is stored in the automatic analysis device A and an adjustment value storage unit 3f of the adjustment system 100.

Figure 5:
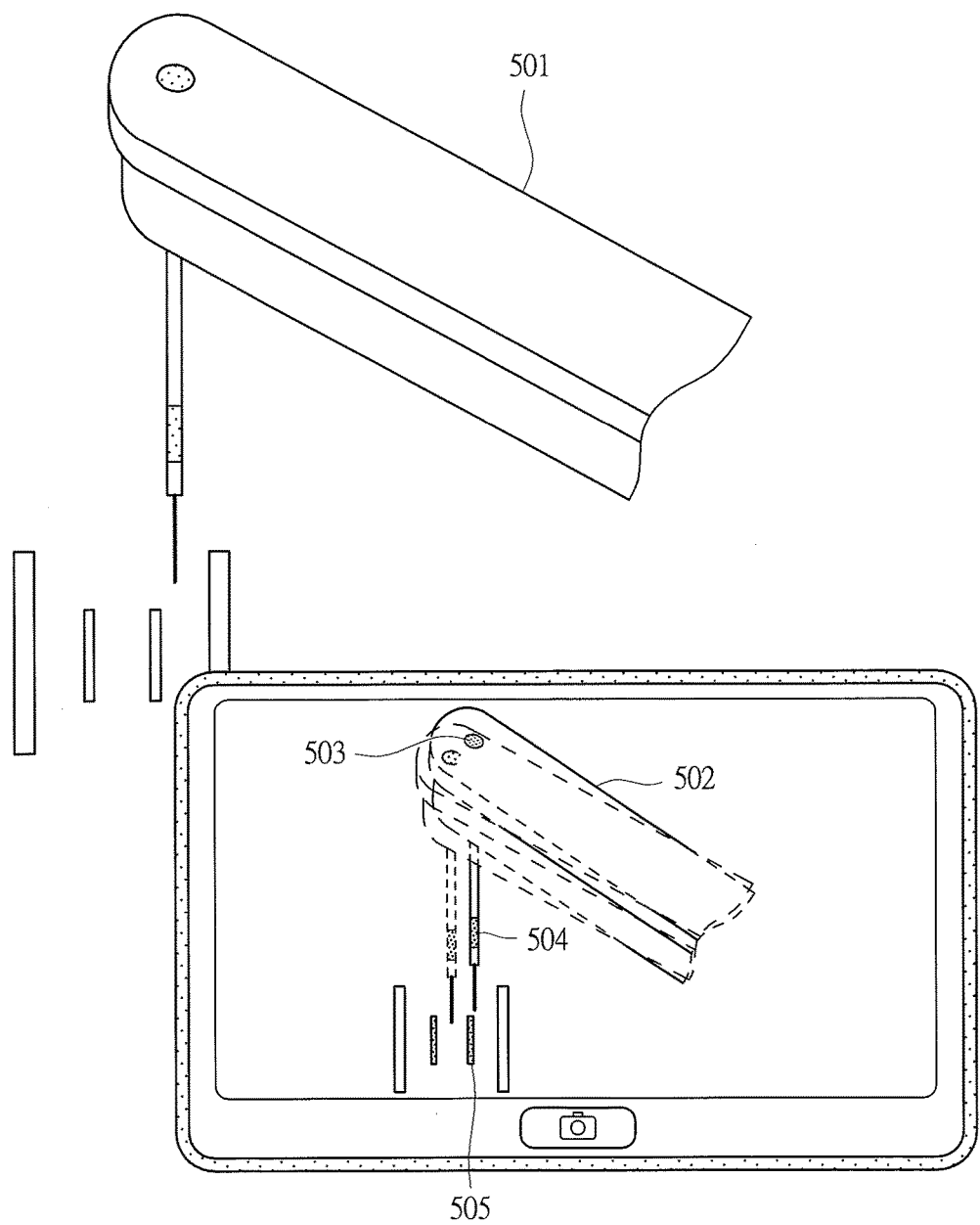
FIG. 5 is a diagram illustrating one example of an image-pickup screen (after an image-pickup) for use in picking up images of the mechanism to be adjusted of the automatic analysis device and the mechanism to be adjusted, and displayed upon picking up images of the mechanism to be adjusted and the portion to be adjusted of the automatic analysis device.

The X/Y axis adjustment direction key 308 and the Z axis adjustment direction key 309 are used for executing the adjustment or "fine adjustment" on the portion to be adjusted where it is not possible to carry out an image pickup process by the camera 60. The X/Y axis adjustment direction key 308 is used for carrying out a horizontal direction movement of the mechanism to be adjusted so as to be made coincident with the portion to be adjusted. The key is also used for carrying out "the fine adjustment" in which picked-up images by the camera 60 of the mechanism to be adjusted and the portion to be adjusted are made coincident with the predetermined position image 306. Referring to FIG. 5, the detailed description thereof will be given.

The Z axis adjustment direction key 309 is used for shifting the mechanism to be adjusted in a vertical direction so as to be position-adjusted to the portion to be adjusted. Additionally, "the fine adjustment" refers to an adjustment process in which, when there is a deviation in the position of the mechanism to be adjusted even after the adjustment value determined by the picked-up image by the camera 60 is reflected to the position of the mechanism to be adjusted, the corresponding deviation is eliminated by using the X/Y axis adjustment direction key 308 and the Z axis adjustment direction key 309.

The adjustment value after determination 310, that is, the adjustment value after completion of the adjustment, is registered in the computer 3 of the automatic analysis device A so that the adjustment values of the automatic analysis device A and the adjustment system 100 are made synchronous to each other. The adjustment value at the time of an adjustment, that is, the adjustment value during the adjustment, is displayed as the adjustment value 311 during the adjustment. At this time, no adjustment value is stored in the automatic analysis device A and the adjustment value storage unit 3f of the computer 3 of the adjustment system 100.

In the case when the image pickup button 305 on the lower portion of the screen is pressed down, a camera mode capable of picking up images of the mechanism to be adjusted and the portion to be adjusted of the automatic analysis device A is turned on so that image pickup processes by the camera 60 are carried out so as to adjust these objects to be adjusted.

Additionally, a small fixed-type camera is attached to an adjustment object, which is invisible from outside, and the portion to be adjusted, which has been selected by the arrow key for use in altering the portion to be adjusted in the adjustment system, is automatically calculated in its adjustment value by pressing down the image pickup button 305 of the adjustment screen, and thereafter, the mechanism of the portion to be adjusted is moved, and upon completion of the adjustment, the adjustment value is transmitted to the adjustment system, and displayed as the adjustment value 310 after determination.

Figure 4:
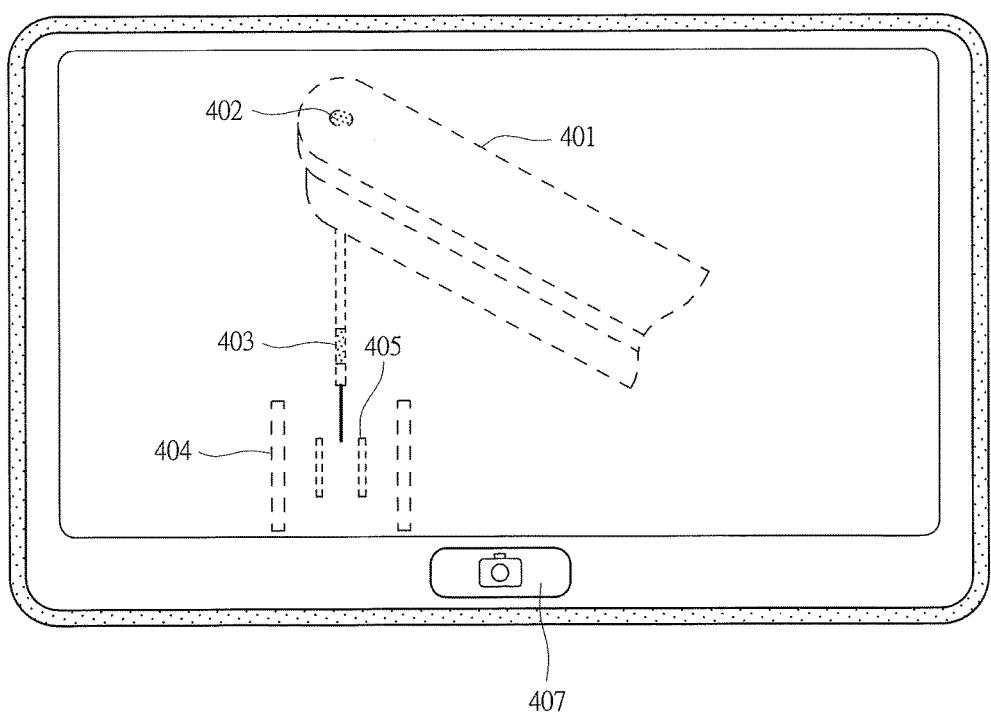
FIG. 4 is a diagram illustrating one example of an image-pickup screen (before an image-pickup) showing the mechanism to be adjusted an image of which is to be picked up, and is displayed upon pressing down an image pickup button of the adjustment screen (FIG. 3) for use in adjusting the mechanism to be adjusted.

FIG. 4 is a diagram illustrating one example of the image pickup screen (prior to the image pickup) for use in picking up the image of the mechanism to be adjusted, which is displayed by the pressing down of the image pickup button 305 of the adjustment screen for use in adjusting the mechanism to be adjusted. The corresponding screen is displayed on the CRT 18 by the computer 3.

On the corresponding screen, the computer 3 displays "a predetermined position image of the mechanism to be adjusted" 401 indicating the predetermined position of the mechanism to be adjusted, "a predetermined position arm identification mark of the mechanism to be adjusted" 402 corresponding to a sign for use in identifying the predetermined position of the arm of the mechanism to be adjusted, "a predetermined position pipetter identification mark of the mechanism to be adjusted" 403 corresponding to a sign for use in identifying the predetermined position of the pipetter when the mechanism to be adjusted is located at the predetermined position and "a predetermined position image of the portion to be adjusted" 404 indicating the predetermined position of the portion to be adjusted.

In the same manner as in the aforementioned adjustment image display area 303 (see FIG. 3) of the adjustment screen of the mechanism to be adjusted, the computer 3 displays the predetermined position image 401 of the mechanism to be adjusted indicating the predetermined position of the mechanism to be adjusted and the predetermined position image 404 of the portion to be adjusted. Onto the arm indicated by the predetermined position image 401 of the mechanism to be adjusted, a predetermined position arm identification mark 402 of the mechanism to be adjusted, which corresponds to a sign for use in identifying the position of the arm located at a predetermined position, is attached.

Moreover, "the predetermined position pipetter identification mark of the mechanism to be adjusted" 403 corresponding to a sign for use in identifying the position of the pipetter located at a predetermined position is included. Furthermore, the predetermined position image 404 of the portion to be adjusted is also provided with a predetermined position washing identification mark 405 for use in allowing the actual portion to be adjusted to be made coincident therewith.

Based upon this screen, images of the mechanism to be adjusted and the portion to be adjusted of the automatic analysis device A are picked up. In the image pickup process, with the identification mark of the portion to be adjusted on the screen and the identification mark of the portion to be adjusted of a subject being made coincident with each other, the image pickup button 407 is pressed down, and when the image pickup process is carried out, the screen of the picked up image screen of the mechanism to be adjusted (after the image pickup) is turned on.

FIG. 5 is a diagram showing the image pickup screen (after the image pickup) for use in picking up the image of the mechanism to be adjusted and the mechanism to be adjusted of the subject on the image pickup screen, which are used upon picking up images of the mechanism to be adjusted and the portion to be adjusted 501 of the automatic analysis device A. The present screen is composed of the mechanism 502 to be adjusted and the arm identification mark 503 of the mechanism to be adjusted as well as the pipetter identification mark 504 of the mechanism to be adjusted and the washing identification mark 505 of the portion to be adjusted.

Below the images of the mechanism to be adjusted and the portion to be adjusted, which are displayed on the image pickup screen of the mechanism to be adjusted, the mechanism to be adjusted and the portion to be adjusted of the subject of the camera 60 are displayed. Upon picking up images of the mechanism to be adjusted and the portion 501 to be adjusted of the automatic analysis device A by using the camera 60 of the present adjustment system, the service person makes the predetermined position washing identification mark 405 of the portion to be adjusted and the washing identification mark (sign for use in identifying an actual object) 505 of the mechanism to be adjusted and the portion to be adjusted 501 of the automatic analysis device A coincident with each other.

After the image pickup process, in order to increase the precision of the matching between the predetermined position washing identification mark 405 of the portion to be adjusted and the mechanism to be adjusted and the portion to be adjusted 501 of the automatic analysis device A, by moving the picked-up images along the X-axis and Y-axis, the images are made coincident with each other by utilizing the X/Y axis adjustment direction key 308 on the picked-up image screen of the mechanism to be adjusted.

With this arrangement, it becomes possible to eliminate an error in the image pickup process caused by service persons. The predetermined position washing identification mark 405 of the portion to be adjusted and the washing identification mark (sign for use in identifying an actual object) 505 of the mechanism to be adjusted and the portion to be adjusted 501 of the automatic analysis device A, thus image-picked up, are made coincident with each other because of the matching process; however, the mechanism to be adjusted 502 that needs to be adjusted deviates from the predetermined position image 401 of the mechanism to be adjusted, which indicates the predetermined position.

In order to indicate this deviation by a numeric value, that is, to calculate an adjustment value, a differential distance d1 between the predetermined position arm identification mark 402 of the mechanism to be adjusted, which is displayed on the screen as data, and the (current position) arm identification mark 503 of the mechanism to be adjusted, which is displayed on the screen as a subject of the camera 60, is measured by analyzing the images; thus, based upon the differential distance d1 measured in this manner, the movement distance (adjustment value) of the mechanism to be adjusted is determined.

Moreover, in order to increase the precision of the movement distance, a differential distance d2 between the predetermined position pipetter identification mark 403 of the mechanism to be adjusted and the pipetter identification mark 504 of the mechanism to be adjusted is measured so that an average value of d1 and d2 is calculated. The value individually obtained forms the movement distance.

FIG. 6 shows a screen including picked up images of the mechanism to be adjusted and the portion to be adjusted, and corresponds to a diagram illustrating processes in detail in which the differential distance between the mechanism to be adjusted and the predetermined position of the mechanism to be adjusted is measured so that the adjustment value is obtained. The differential distance is measured at two portions.

In the arm of the mechanism to be adjusted, a distance between the arm identification mark of the mechanism to be adjusted and the predetermined position arm identification mark of the mechanism to be adjusted is measured in the X-axis direction and the resulting value forms an X-axis adjustment value 601 of the arm of the mechanism to be adjusted, and that measured in the Y-axis direction forms a Y-axis adjustment value 602 of the arm of the mechanism to be adjusted.

By using the same method, in the pipetter of the mechanism to be adjusted, a distance between the pipetter identification mark of the mechanism to be adjusted and the predetermined position pipetter identification mark of the mechanism to be adjusted is measured in the X-axis direction and the resulting value forms an X-axis adjustment value 603 of the pipetter of the mechanism to be adjusted. Moreover, that measured in the Y-axis direction forms a Y-axis adjustment value 604 of the pipetter of the mechanism to be adjusted.

Table 1 shows the respective adjustment values.

TABLE 1

| Section | Adjustment Value of Arm of Mechanism to be Adjusted | Adjustment Value of pipetter of Mechanism to be Adjusted |
| --- | --- | --- |
| X-axis | −4 | −4 |
| Y-axis | −5 | −5 |

Thus, an average value −4 of the X-axis adjustment value −4 of the arm of the mechanism to be adjusted and the X-axis adjustment value −4 of the pipetter of the mechanism to be adjusted forms an adjustment value of the X-axis. Moreover, an average value −5 of the Y-axis adjustment value −5 of the arm of the mechanism to be adjusted and the Y-axis adjustment value −5 of the pipetter of the mechanism to be adjusted forms an adjustment value of the Y-axis.

Each of these adjustment values is displayed as the adjustment value 311 during the adjustment of the manual adjustment/adjustment value display area 304. When the OK button is pressed, with the adjustment value during adjustment being displayed, the adjustment value is determined, and stored in the automatic analysis device A and the adjustment value storage unit 3f of the adjustment system 100. FIG. 7 illustrates a view displayed at this time.

FIG. 7 illustrates a screen given upon completion of the adjustment, which corresponds to the screen displayed when the adjustment value is stored in the automatic analysis device A and the automatic adjustment system.

As explained with reference to FIG. 1A to FIG. 7, in the adjustment system 100 of the automatic analysis device A, the predetermined position image of the mechanism to be adjusted and the predetermined position image of the portion to be adjusted, which indicate correct positions (that is, predetermined positions at which they are located) of the mechanism to be adjusted and the portion to be adjusted whose adjustments are required, are stored.

The predetermined position image of the mechanism to be adjusted and the predetermined position image of the portion to be adjusted are previously stored in a predetermined position information storage unit 25a located in the storage unit 25 of the computer 3 of the adjustment system 100 as information indicating the predetermined position of the adjustment object (see FIG. 1D).

Each of these predetermined position image of the mechanism to be adjusted and predetermined position image of the portion to be adjusted is provided with an identification mark (predetermined position identification mark) for use in identifying the predetermined position of the adjustment object (mechanism to be adjusted/portion to be adjusted), and by using the predetermined position identification mark, it becomes possible to correctly confirm the positions of the mechanism to be adjusted and the portion to be adjusted.

On the other hand, in the adjustment system 100 provided with the camera 60, a mechanism to be adjusted and a portion to be adjusted, which are desirably subjected to adjustment processes, are selected. Predetermined position images of the corresponding mechanism to be adjusted and portion to be adjusted are displayed on the screen. The mechanism to be adjusted and the portion to be adjusted (that is, located at the current positions), which are desirably adjusted, are made coincident with the predetermined position image of the mechanism to be adjusted on the screen, and an image of the adjustment object is picked up by the camera 60.

Current position identification marks that are marks for use in identifying the current position are attached to the objects to be adjusted (mechanism to be adjusted/portion to be adjusted) of the automatic analysis device A, and by picking up images of the objects to be adjusted by the camera 60, the current positions of the objects to be adjusted are identified on the images on the CRT 18.

A current position information acquiring unit 3a (see FIG. 1D) of the computer 3 of the adjustment system 100 acquires the current position image of the adjustment object and the current position identification mark of the adjustment object as pieces of information indicating the current position of the adjustment object.

An adjustment value calculation unit 3c of the computer 3 of the adjustment system 100 compares information indicating the current position of the adjustment object that has been image-picked up by the camera 60 and acquired by the current position information acquiring unit 3a (more specifically, the current position image of the adjustment object and the current position identification mark of the adjustment object) with information indicating the predetermined position of the adjustment object that has been stored in a predetermined position information storage unit 25a (more specifically, the predetermined position image of the adjustment object and the predetermined position identification mark of the adjustment object).

In the above-mentioned example, a distance between the current position identification mark of the mechanism to be adjusted that has been image-picked up by the camera 60 and the predetermined position identification mark on the screen that has been previously stored as data is calculated by the adjustment value calculation unit 3c of the computer 3 and converted into a numeric value so as to be given as an adjustment value of the adjustment object.

Based upon the adjustment value thus calculated, a movement control unit for the adjustment object 3 of the computer 3 moves the mechanism to be adjusted, whose adjustment value has been calculated and which is located at the current position, by a distance corresponding to the adjustment value, so that the mechanism to be adjusted is placed at the predetermined position.

The present adjustment system as described above is used for the automatic analysis device that has been produced and for adjusting and inspecting the respective mechanisms thereof prior to the shipment to a customer. Moreover, at the customer, the present adjustment system can be used in various scenes, such as mechanism adjustments upon installation, regular maintenance jobs, adjustments after exchanging parts at the time of exchanging consumption articles, or the like.

Thus, it becomes possible to eliminate a quality difference as well as a time difference between an experienced person and an inexperienced person.

As described above, specific explanations have been given based upon embodiments of the invention that has been made by the present inventors; however, the present invention is not intended to be limited by the embodiment, and it is needless to say that various modifications may be made therein within a scope not departing from the gist of the present invention.

INDUSTRIAL APPLICABILITY

The present invention is desirably applicable to an automatic analysis device for automatically carrying out an analysis on a sample (for example, a sample (specimen)).

A Automatic analysis device
1 Sample cup
3 Microcomputer
3a Current position information acquiring unit
3c Adjustment value calculation unit
3e Movement control unit for adjustment object
6 Reaction cuvette
8A, 8B Reagent aliquot pipetter
9 Reaction bath
12 Reagent bottle
18 CRT (display device)
25 Storage unit (auxiliary storage device, ROM)
25a Predetermined position information storage unit
60 Camera
100 Adjustment system of automatic analysis device
201 List of mechanisms to be adjusted
202 List of portions to be adjusted
301 Name of mechanism to be adjusted 302 Name of portion to be adjusted
303 Predetermined position image display area of mechanism to be adjusted/portion to be adjusted
305 Image pickup button of mechanism to be adjusted/portion to be adjusted
306 Predetermined position image of mechanism to be adjusted
307 Predetermined position image of portion to be adjusted
310 Adjustment value after determination
311 Adjustment value during adjustment
401 Predetermined position image of mechanism to be adjusted
402 Predetermined position arm identification mark of mechanism to be adjusted
403 Predetermined position pipetter identification mark of mechanism to be adjusted
404 Predetermined position image of portion to be adjusted
405 Predetermined position washing identification mark of portion to be adjusted
501 Mechanism to be adjusted and portion to be adjusted of automatic analysis device A
502 Mechanism to be adjusted
503 Arm identification mark of mechanism to be adjusted
504 Pipetter identification mark of mechanism to be adjusted
505 Washing identification mark of portion to be adjusted
601 Arm X-axis adjustment value of mechanism to be adjusted
602 Arm Y-axis adjustment value of mechanism to be adjusted
603 Pipetter X-axis adjustment value of mechanism to be adjusted
604 Pipetter Y-axis adjustment value of mechanism to be adjusted

The invention claimed is:

1. An adjusting system for adjusting the position of an adjustment object forming a part of an automatic analysis device that automatically carries out an analysis on a sample, the adjusting system comprising:
a predetermined position information memory to previously store information indicating a predetermined position at which the adjustment object should be positioned, including an image indicating the adjustment object located at the predetermined position;
a computer coupled to the adjustment object and the predetermined position information memory, the computer being programmed to
pick up an image of at least one portion of the adjustment object and, based upon the image of the adjustment object, acquire information indicating a current position where the adjustment object is currently located;
by comparing the information indicating the current position of the adjustment object that is obtained with the information indicating a predetermined position of the adjustment object that is stored in the predetermined position information memory, calculate an adjustment value that is a value required for adjusting the position of the adjustment object from the current position to the predetermined position, by comparing the image of the adjustment object located at the current position with the image of the adjustment object located at the predetermined position as superimposed on a same display screen and by indicating the deviation therebetween; and
adjust the position of the adjustment object using the calculated adjustment value;
wherein the adjustment objects includes a movable arm of the automatic analysis device and a pipette connected to the movable arm;
wherein the information indicating the predetermined position at which the adjustment object should be positioned includes a predetermined position of an identification mark on the movable arm;
wherein the information indicating the current position where the adjustment object is currently located includes a current position of the identification mark on the movable arm at a current time;
wherein the information indicating the predetermined position at which the adjustment object should be positioned further includes a predetermined position of an identification mark on the pipette connected to the movable arm, the identification mark on the pipette and the identification mark on the movable arm representing two separate locations of the adjustment object;
wherein the information indicating the current position where the adjustment object is currently located further includes a current position of the identification mark on the pipette connected to the movable arm at the current time; and
wherein the adjustment value is an average of the differential distance between the predetermined position and the current position of the identification mark on the movable arm at the current time and a differential distance between the predetermined position and the current position of the identification mark on the pipette at the current time.

2. The adjusting system for an automatic analysis device according to claim 1,
wherein the computer is programmed to pick up the image of the at least one portion of the adjustment object by using a camera.

3. The adjusting system for an automatic analysis device according to claim 2,
wherein a current position identification mark that is a mark for use in identifying the current position of the adjustment object is attached to the adjustment object, and by picking up an image of the current position identification mark by the camera, the computer is programmed to acquire information indicating the current position of the adjustment object.

4. The adjusting system for an automatic analysis device according to claim 3,
wherein predetermined position identification mark information, which is information corresponding to the current position identification mark and serves as information indicating a predetermined position identification mark in the previously stored predetermined position image for use in identifying the predetermined position of the adjustment object, is previously stored in the predetermined position information memory, and by comparing the position of the current position identification mark in a current position image that has been picked up and the information indicating the predetermined position identification mark, the computer is programmed to calculate the adjustment value.

5. A method for adjusting the position of an adjustment object forming a part of an automatic analysis device that automatically carries out an analysis on a sample, comprising the steps of:
picking up an image of at least one portion of the adjustment object and, based upon the picked upon image and by use of a computer, acquiring information indicating a current position where the adjustment object is currently located;

by comparing the information indicating the current position of the adjustment object thus acquired and information indicating a predetermined position where the adjustment object should be located and which has been stored in the predetermined position memory, calculating an adjustment value that is a value required for adjusting the position of the adjustment object from the current position to the predetermined position;

wherein the predetermined position information memory previously stores an image indicating the adjustment object located at the predetermined position, as said information indicating the predetermined position of the adjustment object;

displaying, superimposed on a same display screen, the image of the adjustment object located at the current position and the image of the adjustment object located at the predetermined position;

wherein the adjustment value is calculated by comparing the image of the adjustment object located at the current position with the image of the adjustment object located at the predetermined position as superimposed on the same display screen and indicating the deviation therebetween; and adjusting the position of the adjustment object using the calculated adjustment value;

wherein the adjustment object includes a movable arm of the automatic analysis device and a pipette connected to the movable arm;

wherein the information indicating the predetermined position at which the adjustment object should be positioned includes a predetermined position of an identification mark on the movable arm;

wherein the information indicating the current position where the adjustment object is currently located includes a current position of the identification mark on the movable arm at a current time;

wherein the information indicating the predetermined position at which the adjustment object should be positioned further includes a predetermined position of an identification mark on the pipette connected to the movable arm, the identification mark on the pipette and the identification mark on the movable arm representing two separate locations of the adjustment object;

wherein the information indicating the current position where the adjustment object is currently located further includes a current position of the identification mark on the pipette connected to the movable arm at the current time; and wherein the adjustment value is an average of the differential distance between the predetermined position and the current position of the identification mark on the movable arm at the current time and a differential distance between the predetermined position and the current position of the identification mark on the pipette at the current time.

6. The adjusting system for an automatic analysis device according to claim 1, wherein the computer is programmed to calculate the adjustment value by comparing the image of the adjustment object located at the current position with the image of the adjustment object located at the predetermined position, including the identification mark on the movable arm and the identification mark on the pipette at the current position and the predetermined position, as displayed on the same display screen and by indicating the deviation therebetween.

7. The method according to claim 5, wherein a camera is used to pick up the image of the at least one portion of the adjustment object.

8. The method according to claim 7, wherein a current position identification mark that is a mark for use in identifying the current position of the adjustment object is attached to the adjustment object; and wherein the information indicating the current position of the adjustment object is acquired by picking up an image of the current position identification mark by the camera.

9. The method according to claim 8, wherein predetermined position identification mark information, which is information corresponding to the current position identification mark and serves as information indicating a predetermined position identification mark in the previously stored predetermined position image for use in identifying the predetermined position of the adjustment object, is previously stored in the predetermined position information memory; and wherein the adjustment value is calculated by comparing the position of the current position identification mark in a current position image that has been picked up and the information indicating the predetermined position identification mark, the computer is programmed to calculate the adjustment value.

10. The method according to claim 5, further comprising:

displaying, on the same display screen, the image of the adjustment object located at the current position and the image of the adjustment object located at the predetermined position, including the identification mark on the movable arm and the identification mark on the pipette at the current position and the predetermined position;

wherein the adjustment value is calculated by comparing the image of the adjustment object located at the current position with the image of the adjustment object located at the predetermined position, including the identification mark on the movable arm and the identification mark on the pipette at the current position and the predetermined position, as displayed on the same display screen and by indicating the deviation therebetween.

11. An adjusting system for adjusting the position of an adjustment object forming a part of an automatic analysis device that automatically carries out an analysis on a sample, the adjusting system comprising:

a computer having a processor and a memory to receive an image of at least one portion of the adjustment object and, based upon the image of the adjustment object, to acquire information indicating a current position where the adjustment object is currently located; and a memory to previously store information indicating a predetermined position at which the adjustment object should be positioned;

a display screen;

wherein the processor of the computer is coupled to the adjustment object, the memory, and the display screen, and is programmed, by comparing the information indicating the current position of the adjustment object that is obtained by the computer acquiring the information indicating the current position with the information indicating a predetermined position of the adjustment object that is stored in the memory storing the predetermined position information, to calculate an adjustment value that is a value required for adjusting the position of the adjustment object from the current position to the predetermined position;

wherein the memory has previously stored therein an image indicating the adjustment object located at the predetermined position, as said information indicating the predetermined position of the adjustment object;

wherein the computer processor is programmed to calculate the adjustment value by comparing the image of the adjustment object located at the current position with the image of the adjustment object located at the predetermined position as superimposed on the same display screen and by indicating the deviation therebetween;

wherein the computer processor is programmed to adjust the position of the adjustment object using the calculated adjustment value;

wherein the adjustment object includes a movable arm of the automatic analysis device and a pipette connected to the movable arm;

wherein the information indicating the predetermined position at which the adjustment object should be positioned includes a predetermined position of an identification mark on the movable arm;

wherein the information indicating the current position where the adjustment object is currently located includes a current position of the identification mark on the movable arm at a current time; and wherein the information indicating the predetermined position at which the adjustment object should be positioned further includes a predetermined position of an identification mark on the pipette connected to the movable arm, the identification mark on the pipette and the identification mark on the movable arm representing two separate locations of the adjustment object;

wherein the information indicating the current position where the adjustment object is currently located further includes a current position of the identification mark on the pipette connected to the movable arm at the current time; and wherein the adjustment value is an average of the differential distance between the predetermined position and the current position of the identification mark on the movable arm at the current time and a differential distance between the predetermined position and the current position of the identification mark on the pipette at the current time.

12. The adjusting system according to claim 11, further comprising:

a camera to pick up the image of the at least one portion of the adjustment object and provide the image to the computer processor;

wherein a current position identification mark that is a mark for use in identifying the current position of the adjustment object is attached to the adjustment object, and by picking up an image of the current position identification mark by the camera, the computer processor is programmed to acquire information indicating the current position of the adjustment object.

13. The adjusting system according to claim 12, wherein predetermined position identification mark information, which is information corresponding to the current position identification mark and serves as information indicating a predetermined position identification mark in the previously stored predetermined position image for use in identifying the predetermined position of the adjustment object, is previously stored in the predetermined position information memory, and by comparing the position of the current position identification mark in a current position image that has been picked up and the information indicating the predetermined position identification mark, the computer processor is programmed to calculate the adjustment value.

14. The adjusting system according to claim 11, wherein the computer processor is programmed to calculate the adjustment value by comparing the image of the adjustment object located at the current position with the image of the adjustment object located at the predetermined position, including the identification mark on the movable arm and the identification mark on the pipette at the current position and the predetermined position, as displayed on the same display screen and by indicating the deviation therebetween.

* * * * *